United States Patent [19]

Hoelderich et al.

[11] 4,434,314

[45] Feb. 28, 1984

[54] PREPARATION OF OLEFINS FROM METHANOL/DIMETHYL ETHER

[75] Inventors: Wolfgang Hoelderich; Wolf D. Mross, both of Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 417,523

[22] Filed: Sep. 13, 1982

[30] Foreign Application Priority Data

Sep. 17, 1981 [DE] Fed. Rep. of Germany ....... 3136984

[51] Int. Cl.³ .............................................. C07C 1/00
[52] U.S. Cl. .................................................. 585/640
[58] Field of Search ........................................ 585/640

[56] References Cited

U.S. PATENT DOCUMENTS

| 3,894,107 | 7/1975 | Butter et al. | 585/640 |
| 4,025,575 | 5/1977 | Chang et al. | |
| 4,207,424 | 6/1980 | Winnick | 585/640 |
| 4,292,458 | 9/1981 | Klotz | 585/640 |
| 4,359,595 | 11/1982 | Rollmann | 585/640 |

FOREIGN PATENT DOCUMENTS 2615150 10/1976 Fed. Rep. of Germany .

Primary Examiner—Curtis R. Davis
Attorney, Agent, or Firm—John H. Shurtleff

[57] ABSTRACT

A process for the preparation of olefins from methanol and/or dimethyl ether by conversion in the presence of a zeolite catalyst, in particular a borosilicate zeolite, at elevated temperature, with the addition of a small amount of an electron donor.

10 Claims, No Drawings

PREPARATION OF OLEFINS FROM METHANOL/DIMETHYL ETHER

Efforts to prepare olefins from methanol have recently become of increasing interest. Methanol can be prepared from coal, by coal gasification, and from synthesis gas, by established technologies. If it were possible to convert methanol into lower olefins in an economical manner, the methods of further processing which are customary in the chemical industry today could be retained if coal were to be used as the raw material. In past years processes have therefore been developed aimed at preparing olefins from methanol and/or dimethyl ether. Such a process is disclosed in, for example, German Laid-Open Application DOS No. 2,615,150. The reaction can be optimized by various measures, for example by shortening the residence time. Other measures which promote formation of olefins are, in particular, dilution of the methanol and/or dimethyl ether with inert gases and/or steam, or dilution of the catalyst with binders.

We have found that a high yield of $C_2$-$C_4$-olefins is obtained from methanol and/or dimethyl ether by conversion in the presence of a zeolite catalyst at elevated temperatures if the conversion is carried out in the presence of a small amount of an electron donor.

For the purposes of the invention, examples of electron donors which are added to the starting materials are the classes of substances listed below. Substances which have a Lewis basicity are generally suitable as electron donors.

The particular technical effect achieved by the addition of electron donors to the starting substances before the reaction over zeolite catalysts is that of increasing the selectivity and the catalyst life. The selectivity is increased in the sense of increased formation of olefins, in particular ethylene, propylene and butenes. The $C_5^+$ hydrocarbon content of the reaction product is decreased.

In a preferred embodiment of the process according to the invention, from 1 to 300 ppm, in particular from 1 to 10 ppm, of an electron donor are added to the methanol, and the mixture is reacted over a borosilicate zeolite at from atmospheric pressure to 30 bar, and at from 300° to 700° C., preferably from 400° to 550° C.

The starting materials, eg. the methanol, can have a water content of not more than 90% by weight. Crude methanol, such as is obtained from the synthesis reaction and contains about 20% by weight of water is preferably used. Other lower alcohols can also be admixed to the methanol. The throughput over the catalyst, expressed as the weight hourly space velocity in $h^{-1}$—g of methanol and/or dimethyl ether per g of catalyst per hour - is advantageously chosen so that conversion is substantially quantitative and no separation problems and recycling problems arise. The weight hourly space velocity is therefore generally from 0.5 to 50 $h^{-1}$, preferably from 2 to 15 $h^{-1}$. A particular advantage of the invention is that the conversion of crude methanol or dimethyl ether to $C_2$-$C_4$-olefins can be carried out in the absence of a diluent.

The compounds which follow are examples of electron donors which can be added to the starting materials:

1. Substituted hydrocarbons of the formulae $X_n(CR^1R^2)_qY_m$, $X_nCY_mZ_l$ and $X_nY_mZ_lC$-$(R)_{4-m-n-l}$ where X is F, Cl, Br, I, H, O, S or N, Y is F, Cl, Br, I, H, O, S or N, Z is F, Cl, Br, I, H, O, S or N, R, $R^1$ and $R^2$ are identical or different and each is hydrogen, alkyl, such as $CH_3$— or $C_2H_5$—, alkoxy, such as $CH_3O$— or $C_2H_5O$—, alkylcarbonyl, such as —CO—$CH_3$ or —CO—$C_2H_5$, an acid group, such as —COOH, an ester group, such as —COOCH$_3$ or —COOC$_2$H$_5$, or amino, such as —N(CH$_3$)$_2$ or —N(C$_2$H$_5$)$_2$, l is from 1 to 4, m is from 1 to 4, n is from 1 to 4 and q is from 1 to 10.

2. Other suitable substituted hydrocarbons, ie. organic acids and amines.

3. Substituted silanes of the formulae $X_n(SiR_2)_qY_m$, $X_nSiY_mZ_l$ and $X_nY_mZ_lSiR_{4-n-m-l}$ where X is F, Cl, Br, I or H, Y is F, Cl, Br, I or H, R is hydrogen, alkyl, such as $CH_3$— or $C_2H_5$—, alkoxy, such as $CH_3O$— or $C_2H_5O$—, alkylcarbonyl, such as —CO—$CH_3$ or —CO—$C_2H_5$, an acid group, such as —COOH, an ester group, such as —COOCH$_3$, or amino, such as —N(CH$_3$)$_2$ or —N(C$_2$H$_5$)$_2$, l is from 1 to 4, m is from 1 to 4, n is from 1 to 4 and q is from 1 to 4.

4. Other suitable silicon-containing compounds, ie. siloxanes, such as disiloxanes and trisiloxanes, silylamines, such as trimethylsilylamine, silylphosphines, such as trimethylsilylphosphine, and silicic acids and esters thereof.

5. Substituted sulfur compounds of the formulae $X_nSY_m$ and $X_nY_mSR_{6-m-n}$ where X is F, Cl, Br, I, H or O, Y is F, Cl, Br, I, H or O, R is, for example, hydrogen, alkyl or alkoxy, m is from 1 to 6 and n is from 1 to 6.

6. Other suitable sulfur compounds, ie. acids of sulfur and esters thereof.

7. Substituted P, As and Sb compounds of the formulae $X_mY_nZ_lPR_{5-m-n-l}$, $X_mY_nZ_lAsR_{5-m-n-l}$ and $X_mY_nZ_lSbR_{5-m-n-l}$ where X is F, Cl, Br, I, H, O or S, Y is F, Cl, Br, I, H, O or S, Z is F, Cl, Br, I, H, O or S, R is hydrogen, alkyl, alkoxy, amino, such as —N(CH$_3$)$_2$, or phosphino, such as —P(CH$_3$)$_2$, l is from 1 to 5, m is from 1 to 5 and n is from 1 to 5.

8. Other suitable phosphorus, arsenic and antimony compounds, ie. the acids of these elements and esters thereof, as well as alkyl, aryl and alkoxy compounds of these elements.

The Examples which follow illustrate the process according to the invention.

EXAMPLE 1

The boron zeolite is prepared by hydrothermal synthesis from 66.1 g of $SiO_2$ and 30.8 g of $H_3BO_3$ in 881 g of an aqueous propane-1,3-diamine solution (50:50 mixture) at 170° C. under autogenous pressure in a stirred autoclave. The crystalline product is filtered off, washed, dried at 160° C. for 24 hours and calcined at 500° C. for 24 hours. The borosilicate zeolite formed is composed of 91.2% of $SiO_2$ and 4.74% of $B_2O_3$. The zeolite catalyst used in the Examples which follow is obtained by extruding the above zeolite with boehmite in a ratio of 60:40.

EXAMPLES 2-5

In Examples 2-5, crude methanol is converted to olefins over the catalyst desribed above, with or without the additon of dichloroethane to the starting materials (Table 1). The reaction is carried out at 450° C. and a weight hourly space velocity of 7.8 $h^{-1}$. Conversion of the methanol is quantitative.

TABLE 1

Effect of the dichloroethane

| Example | 2 | 3 | 4 |
|---|---|---|---|
| ClCH$_2$—CH$_2$Cl | — | 1 ppm | 5 ppm |
| CH$_4$ | 2.0% | 2.5% | 2.6% |
| C$_2$H$_4$ | 7.6% | 9.3% | 9.0% |
| C$_2$H$_6$ | 0.2% | 0.2% | 0.3% |
| C$_3$H$_6$ | 32.5% | 37.2% | 36.4% |
| C$_3$H$_8$ | 2.1% | 2.8% | 2.7% |
| C$_4$H$_8$ | 22.5% | 26.5% | 28.8% |
| C$_4$H$_{10}$ | 5.2% | 6.5% | 5.3% |
| C$_5$+ | 25% | 13.8% | 13.5% |
| ΣC | 97.1% | 98.8% | 98.6% |
| g of CH$_3$OH/g of catalyst | 320 g | 304 g | 390 g |

The percentages given indicate the yields of hydrocarbons, based on CH$_2$ employed.

Table 1 shows that the addition of dichloroethane has a positive effect on the selectivity of the conversion of methanol to C$_2$–C$_4$-olefins. The life of the catalyst up to its first regeneration is also increased by the addition.

EXAMPLES 6–12

In Examples 6 to 12, crude methanol to which various electron donors have been added is converted to lower olefins at 500° C. and at a weight hourly space velocity of 7.8 h$^{-1}$ (Table 2). Conversion of the methanol is complete.

TABLE 2

Effect of various electron donors

| Example | 6 | 7 | 8 | 9 | 10 | 11 | 12 |
|---|---|---|---|---|---|---|---|
| Additive | — | CCl$_4$ | HCl | CH$_2$Cl$_2$ | SOCl$_2$ | Freon 12 | (CH$_3$)$_3$SiF |
| CH$_4$ | 3.7% | 3.9% | 4.3% | 5.0% | 5.2% | 3.9% | 4.8% |
| C$_2$H$_4$ | 9.5% | 10.9% | 10.9% | 10.2% | 11.0% | 11.0% | 10.3% |
| C$_2$H$_6$ | 0.3% | 0.4% | 0.3% | 0.4% | 0.4% | 0.4% | 0.4% |
| C$_3$H$_6$ | 36.9% | 42.8% | 42.2% | 40.6% | 40.3% | 40.2% | 40.0% |
| C$_3$H$_8$ | 1.2% | 1.9% | 1.9% | 1.7% | 2.0% | 2.2% | 1.7% |
| C$_4$H$_8$ | 17.3% | 25.9% | 24.0% | 24.3% | 24.6% | 22.5% | 24.1% |
| C$_4$H$_{10}$ | 1.5% | 2.3% | 2.3% | 2.4% | 2.5% | 3.9% | 2.8% |
| C$_5$+ | 29.0% | 8.0% | 9.4% | 11.6% | 10.7% | 11.9% | 10.7% |

The values given indicate the yields of hydrocarbons, based on CH$_2$ employed.

In Table 2, also, the drop in the C$_5$+ content, in particular, shows the effect of the electron donors in increasing the selectivity in the sense of increased formation of ethylene, propylene and butenes.

We claim:

1. In a process for the preparation of olefins from methanol and/or dimethyl ether by conversion in the presence of a zeolite catalyst at elevated temperature, the improvement which comprises:
   carrying out the reaction with the addition of a small amount of about 1 to 300 ppm of a substance which has a Lewis basicity as an electron donor.

2. A process as claimed in claim 1, wherein the reaction is carried out in the presence of a borosilicate zeolite.

3. A process as claimed in claim 1 or 2, wherein a substituted hydrocarbon is added to the starting materials as said electron donor.

4. A process as claimed in claim 1 or 2, wherein an organic acid or amine is added to the starting substances as said electron donor.

5. A process as claimed in claim 1 or 2, wherein a substituted silane is added to the starting materials as said electron donor.

6. A process as claimed in claim 1 or 2, wherein a silicon-containing compound, which is a siloxane, disiloxane, trisiloxane, silylamine, silylphosphine, or silicic acid or an ester thereof, is added to the starting materials as said electron donor.

7. A process as claimed in claim 1 or 2, wherein a substituted sulfur compound or an acid of sulfur or ester thereof is added to the starting substances as an electron donor.

8. A process as claimed in claim 1 or 2, wherein a substituted P, As or Sb compound is added to the starting substances as said electron donor.

9. A process as claimed in claim 1 or 2, wherein a phosphorus, arsenic or antimony compound, which is an acid of one of these elements or an ester thereof, or an alkyl, aryl or alkoxy compound of one of these elements, is added to the starting substances as said electron donor.

10. A process as claimed in claim 1 or 2, wherein the electron donor is added to the starting materials in an amount of from 1 to 10 ppm.

* * * * *